(12) United States Patent
Gunderson et al.

(10) Patent No.: US 8,792,971 B2
(45) Date of Patent: Jul. 29, 2014

(54) METHOD AND APPARATUS FOR IDENTIFYING OVERSENSING USING FAR-FIELD INTRACARDIAC ELECTROGRAMS AND MARKER CHANNELS

(71) Applicant: Medtronic, Inc., Minneapolis, MN (US)

(72) Inventors: Bruce D. Gunderson, Plymouth, MN (US); Amisha S. Patel, Apex, NC (US); Chad A. Bounds, Minneapolis, MN (US); Mark L. Brown, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 13/668,673

(22) Filed: Nov. 5, 2012

(65) Prior Publication Data
US 2013/0060117 A1    Mar. 7, 2013

Related U.S. Application Data

(63) Continuation of application No. 12/476,733, filed on Jun. 2, 2009, now Pat. No. 8,386,024, which is a continuation of application No. 11/108,472, filed on Apr. 18, 2005, now Pat. No. 7,567,835.

(51) Int. Cl.
*A61B 5/0456* (2006.01)
*A61B 5/0464* (2006.01)
*A61N 1/362* (2006.01)
*A61N 1/37* (2006.01)

(52) U.S. Cl.
CPC ............ *A61B 5/0456* (2013.01); *A61N 1/3622* (2013.01); *A61N 1/3702* (2013.01); *A61B 5/0464* (2013.01)

USPC ............. 600/518; 600/515; 600/519; 607/14

(58) Field of Classification Search
None
See application file for complete search history.

(56) References Cited

U.S. PATENT DOCUMENTS

| | | |
|---|---|---|
| 4,374,382 A | 2/1983 | Markowitz |
| 5,193,535 A | 3/1993 | Bardy et al. |
| 5,381,803 A | 1/1995 | Herleikson et al. |
| 5,388,586 A | 2/1995 | Lee et al. |
| 5,545,186 A | 8/1996 | Olson et al. |
| 5,558,098 A | 9/1996 | Fain |
| 6,029,087 A | 2/2000 | Wohlgemuth |
| 6,067,473 A | 5/2000 | Greeninger et al. |
| 6,070,097 A | 5/2000 | Kreger et al. |
| 6,526,311 B2 | 2/2003 | Begemann |
| 6,539,259 B1 | 3/2003 | Weinberg et al. |
| 6,650,931 B1 | 11/2003 | McClure et al. |
| 6,934,585 B1 | 8/2005 | Schloss et al. |

(Continued)

FOREIGN PATENT DOCUMENTS

| | | |
|---|---|---|
| WO | 2004084722 | 10/2004 |
| WO | 2004093974 | 11/2004 |

*Primary Examiner* — Kennedy Schaetzle
(74) *Attorney, Agent, or Firm* — Michael J. Ostrom; Stephen W. Bauer

(57) ABSTRACT

A method for identifying oversensing in implantable medical devices (IMDs), such as implantable cardioverter defibrillators (ICDs), is described. A near-field electrogram signal and a far-field electrogram signal are obtained via a near-field electrode pair and a far-field electrode pair. The near-field electrogram signal is compared to the far-field electrogram signal and a determination of whether oversensing exists is made based on the comparison. In some instances, a scheduled therapy is withheld in response to determining that oversensing exists.

8 Claims, 14 Drawing Sheets

(56) References Cited

U.S. PATENT DOCUMENTS

| | | |
|---|---|---|
| 7,139,604 B1 | 11/2006 | Mouchawar et al. |
| 7,567,835 B2 | 7/2009 | Gunderson et al. |
| 2002/0091333 A1 | 7/2002 | Hsu et al. |
| 2004/0015197 A1 | 1/2004 | Gunderson |
| 2004/0186388 A1 | 9/2004 | Gerasimov |
| 2004/0210147 A1 | 10/2004 | Houben |
| 2004/0230233 A1 | 11/2004 | Gunderson et al. |
| 2005/0004607 A1 | 1/2005 | Bjorling |
| 2006/0116730 A1* | 6/2006 | Gunderson .................. 607/17 |
| 2006/0161205 A1 | 7/2006 | Mitrani et al. |

* cited by examiner

METHOD AND APPARATUS FOR IDENTIFYING OVERSENSING USING FAR-FIELD INTRACARDIAC ELECTROGRAMS AND MARKER CHANNELS

RELATED APPLICATION

This application is a continuation application of U.S. patent application Ser. No. 12/476,733, filed Jun. 2, 2009 (now published as U.S. Published Application No. 2009/0292331 A1), which is a continuation application of U.S. patent application Ser. No. 11/108,472, filed Apr. 18, 2005 (now granted U.S. Pat. No. 7,567,835).

FIELD

The invention relates to a method and apparatus for automatically identifying and classifying oversensing of cardiac and non-cardiac events by an implantable cardiac device using intracardiac electrogram signals.

BACKGROUND

Implantable medical devices are available to provide therapies for restoring normal cardiac rhythms by delivering electrical shock therapy for cardioverting or defibrillating the heart, in addition to providing cardiac pacing. Such a device, commonly known as an implantable cardioverter defibrillator ("ICD") senses a patient's heart rhythm and may classify the rhythm according to a number of programmable rate zones in order to detect episodes of tachycardia or fibrillation. Single chamber devices are available for treating either atrial arrhythmias or ventricular arrhythmias, and dual chamber devices are available for treating both atrial and ventricular arrhythmias. Rate zone classifications may include slow tachycardia, fast tachycardia, and fibrillation.

Upon detecting an abnormal rhythm, the ICD may select and deliver a therapy based upon detected rate and/or other programmable criteria, for example. Cardiac pacing may be delivered in response to the absence of sensed intrinsic depolarizations within a specified time window, referred to as P-waves in the atrium and R-waves in the ventricle. In response to tachycardia detection, a number of tiered therapies may be delivered beginning with anti-tachycardia pacing therapies and possibly escalating to more aggressive therapies until the tachycardia is terminated. Termination of a tachycardia is commonly referred to as "cardioversion." Ventricular fibrillation (VF) is a serious life-threatening condition and is normally treated by delivering high-energy shock therapy. Termination of VF in this manner is normally referred to as "defibrillation."

In many currently available ICDs, a physician or operator has the ability to program particular anti-arrhythmia therapies into the device ahead of time, and a menu of therapy options is typically provided. For example, on initial detection of an atrial or ventricular tachycardia, an anti-tachycardia pacing therapy may be selected and delivered to the chamber or chambers in which the tachycardia is diagnosed. After the initial therapy is delivered, a subsequent redetection of tachycardia may lead to a more aggressive anti-tachycardia pacing therapy, for example. If repeated attempts at anti-tachycardia pacing therapies fail, a cardioversion or defibrillation shock may next be selected. For an overview of tachycardia detection and treatment therapies, reference is made to U.S. Pat. No. 5,545,186 issued to Olson et al.

Detection of tachycardia or fibrillation may also trigger the storage of sensed intracardiac electrograms (EGMs) for a period of time such that the EGM signals leading up to and during a detected arrhythmia episode may be available for downloading from the ICD and displaying on an external programmer or other device for analysis by a physician. Such analysis of stored EGM signals may aid the physician in monitoring the status of the patient and the patient's response to delivered therapies. Occasionally, an ICD may inappropriately detect a tachycardia or fibrillation episode that does not exist physiologically, and may deliver an anti-arrhythmia therapy when one is not needed or desired. Inappropriate arrhythmia detections may, in some cases, cause a patient to experience painful, repeated cardioversion or defibrillation shocks within a relatively short period of time. Certain therapies delivered inappropriately, for example during normal sinus rhythm, can potentially induce an arrhythmia in some patients. For these reasons, the delivery of a therapy in response to inappropriate arrhythmia detection is highly undesirable.

Inappropriate arrhythmia detection may be caused by "oversensing." Oversensing may be defined as the sensing or detection of cardiac events other than what should be expected for a given physiological condition. Oversensing of both cardiac and non-cardiac events can result in inappropriate arrhythmia detection by the ICD if the detected rate due to oversensing falls into an arrhythmia detection rate zone. Cardiac oversensing typically refers to oversensing of cardiac events such as far-field R-waves, T-waves, or R-waves that are sensed twice and are therefore "double-counted." Examples of cardiac oversensing are illustrated in FIG. 1. A conventional electrocardiogram ("ECG") signal is illustrated showing a normal cardiac cycle indicated by a P-wave, R-wave, and T-wave. Beneath the ECG is a representation of a ventricular intracardiac electrogram signal (VEGM) in which a ventricular signal spike coincides in time with the R-wave on the ECG. During normal sensing, a patient in normal sinus rhythm will exhibit one atrial sensed event ($A_S$) and one ventricular sensed event ($V_S$) during each cardiac cycle, corresponding to the atrial P-wave and the ventricular R-wave, respectively, as indicated by the marker channel labeled "Normal Sensing" (shown beneath the VEGM). The VEGM is typically obtained by recording inputs from a pair of relatively closely-spaced electrodes located in proximity to a ventricle of the heart. Signals from such closely-spaced electrodes are sometimes referred to as "near-field" electrogram (NF EGM) signals. The spacing of electrodes for obtaining NF EGM signals may be determined, for example, by the tip-to-ring electrode spacing of commonly used bipolar electrodes, as are known in the art.

Far-field R-wave oversensing (sensing of ventricular depolarizations by the atrial lead) is illustrated in FIG. 1. In the marker channel labeled "Far Field R-wave Oversensing," two atrial sensed events ($A_S$) are indicated during each cardiac cycle. One atrial sensed event ($A_S$) per cardiac cycle corresponds to the appropriate sensing of a P-wave, while a second atrial sensed event ($A_S$) per cardiac cycle corresponds to the far-field sensing of the R-wave. Far-field R-waves are sometimes sensed on the atrial EGM (not shown) because the amplitude of an R-wave, as sensed at the atrial sensing electrodes, may reach or exceed the atrial sensitivity threshold. Therefore, an atrial sensitivity setting that appropriately senses P-waves may sometimes also result in inappropriate sensing of far-field R-waves from the ventricles (i.e., oversensing).

T-wave oversensing is also illustrated in FIG. 1. In the marker channel labeled "T-wave Oversensing," two ventricular sensed events ($V_S$) are shown occurring during each cardiac cycle, one coinciding in time with the R-wave and one coinciding in time with the T-wave. T-wave oversensing may occur when the ventricular sensitivity setting is too sensitive, for example, resulting in sensing of both R-waves and T-waves. T-wave oversensing may also occur when the R-wave amplitude has decreased sufficiently to cause the "auto-adjusting threshold," which varies the ventricular sensitivity setting as a function of the sensed R-wave amplitude, to decrease below the T-wave amplitude. R-wave oversensing, also referred to as "R-wave double-counting," is also illustrated in FIG. 1 in which two ventricular sense events ($V_S$) correspond to a single R-wave. This "double-counting" of R-waves can occur, for example, when an R-wave complex is widened due to conditions such as bundle branch block or wide complex ventricular tachycardia. For each of the above-described types of cardiac oversensing, generally one extra atrial or ventricular sensed event may be detected per cardiac cycle, as seen in the illustrations of FIG. 1.

Non-cardiac oversensing refers to undesired sensing by an ICD of electrical signals that are not cardiac in origin. Such non-cardiac signals are sometimes referred to as "noise." Noise may occur in the form of myopotentials (electrical signals generated by surrounding muscle tissue) or as the result of electromagnetic interference ("EMI") from sources external to the patient. Noise may also occur when the insulation of a lead fails, when a lead conductor becomes fractured, or when a lead is poorly connected to the ICD.

Examples of non-cardiac oversensing are illustrated in FIGS. 2A through 2C. In FIG. 2A, a ventricular EGM signal is shown with a corresponding illustration of electromagnetic interference (EMI) oversensing. EMI appears as relatively continuous high frequency noise on the VEGM and can be repeatedly detected as a ventricular sensed event ($V_S$) by the ICD. In FIG. 2B, a ventricular EGM is shown with a corresponding illustration of myopotential oversensing. Myopotentials may appear as noise on the VEGM at lower frequencies than EMI, resulting in somewhat less frequent but repeated ventricular sensed events ($V_S$). In FIG. 2C, a ventricular EGM is shown corresponding to noise associated with a lead fracture or a poor lead connection. This type of noise can result in saturation of the sense amplifiers and intermittent bursts of noise. Oversensing due to a lead fracture or poor lead connection, therefore, may produce intermittent clusters of ventricular sensed events ($V_S$), as shown in FIG. 2C. As seen in FIGS. 2A through 2C, non-cardiac oversensing is generally associated with multiple oversensed events in an affected cardiac cycle, and may be intermittent or continuous, of high or low amplitude, and of relatively low or high frequency.

Since the various types of oversensing may occur relatively infrequently and are not routinely encountered in all patients, the task of recognizing and trouble-shooting oversensing conditions can be a challenging one to the physician. Oversensing may not be recognized until inappropriate arrhythmia detections are made and/or unneeded therapies delivered. While stored EGM data can be useful in identifying and trouble-shooting inappropriate arrhythmia detections due to oversensing, valid arrhythmia detections may occur the majority of the time with only an occasional inappropriate detection occurring; this may make the task of identifying the cause of inappropriate detections from analysis of stored EGM episode data a difficult and time-consuming task. Once an inappropriate detection is identified, the numerous types of oversensing that may have caused the inappropriate detection make diagnosing the problem complex. With a growing number of ICD patients in broad geographical distributions, clinicians need to be able to quickly and confidently diagnose and correct such problems. What is needed, therefore, is an automated method for recognizing oversensing and specifically identifying the type of oversensing present so that a physician may make prompt corrective actions with confidence.

SUMMARY

Certain embodiments of the invention provide methods of detecting the occurrence of intrinsic depolarizations within a heart chamber by analysis of far-field electrogram (EGM) signals.

Certain embodiments of the invention provide a method of evaluating EGM data to determine if oversensing is present and, if so, determining the most likely cause of oversensing. Far-field EGM (FF EGM) signals may be analyzed and compared to sensed events detected from near-field EGM (NF EGM) signals. The analysis may also include examination of signal morphology using template matching to classify certain types of oversensing. Various types of cardiac oversensing that may be identified include, but are not limited to, far-field R-wave oversensing, R-wave oversensing, and T-wave oversensing. Non-cardiac causes of oversensing that may be diagnosed include electromagnetic interference (EMI), non-cardiac myopotentials, a lead fracture, or a poor lead connection.

Certain embodiments of the invention include a method of identifying an inappropriate arrhythmia detection due to oversensing. Further embodiments include a method of classifying the type of oversensing resulting in inappropriate arrhythmia detection.

Certain embodiments of the invention may be adapted for use in external devices (e.g., programmers, personal computers, CareLink) for offline processing of EGM data that has been stored in an implantable medical device (IMD) and transferred to the external device.

Certain embodiments of the invention may be adapted for use in IMDs, including implantable monitors, ICDs or pacemakers for either post-processing or real-time processing of EGM data. Further embodiments of the invention may include IMDs that automatically adjust programmable settings in response to processing of EGM data.

DRAWINGS

DESCRIPTION

Figure 1:
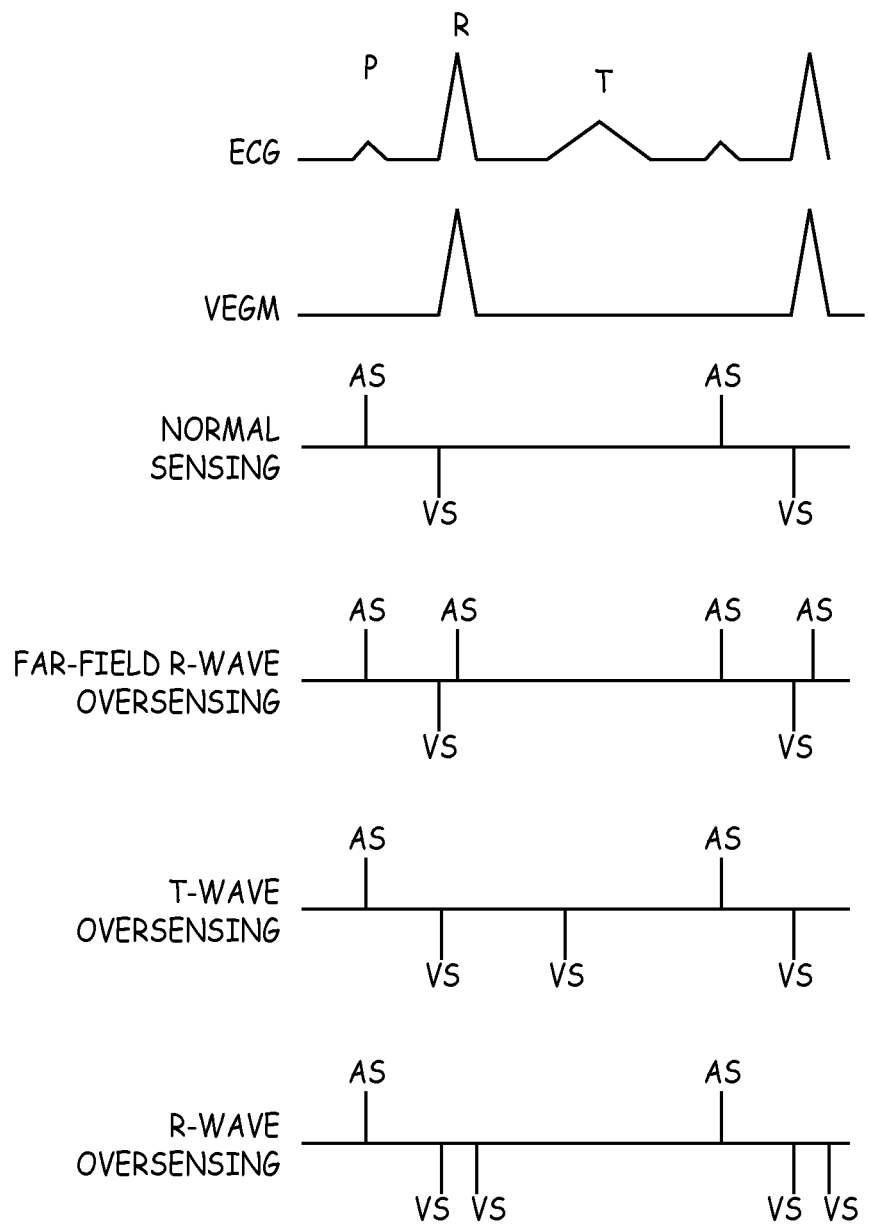
FIG. 1 is an illustration of an ECG signal, a corresponding ventricular EGM (VEGM) signal, and corresponding representations of sensed events (marker channels) occurring during normal sensing, far-field R-wave oversensing, T-wave oversensing, and R-wave oversensing.
Figure 2A:
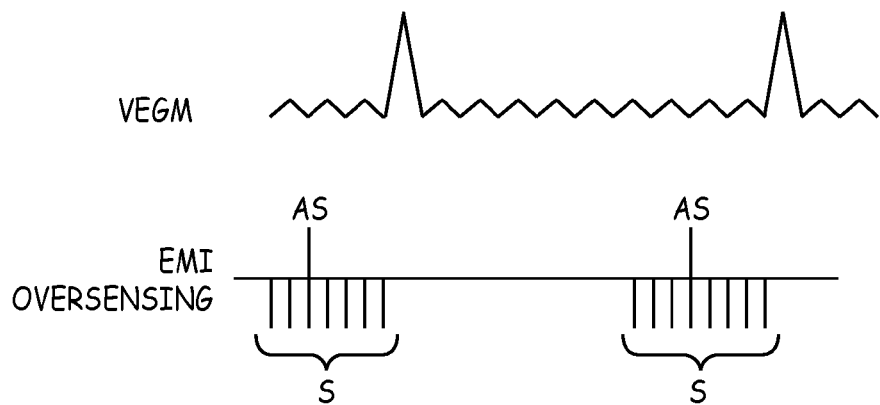
FIG. 2A is an illustration of a ventricular EGM (VEGM) signal with noise due to electromagnetic interference (EMI) and a corresponding marker channel during EMI oversensing.
Figure 2B:
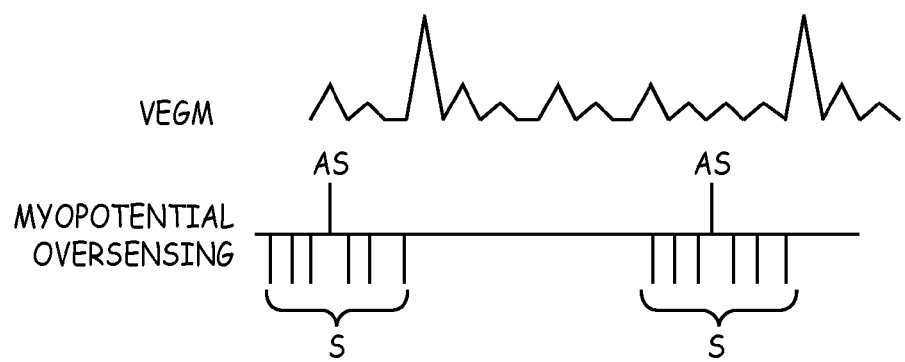
FIG. 2B is an illustration of a ventricular EGM (VEGM) signal with myopotential noise and a corresponding marker channel during myopotential oversensing.
Figure 2C:
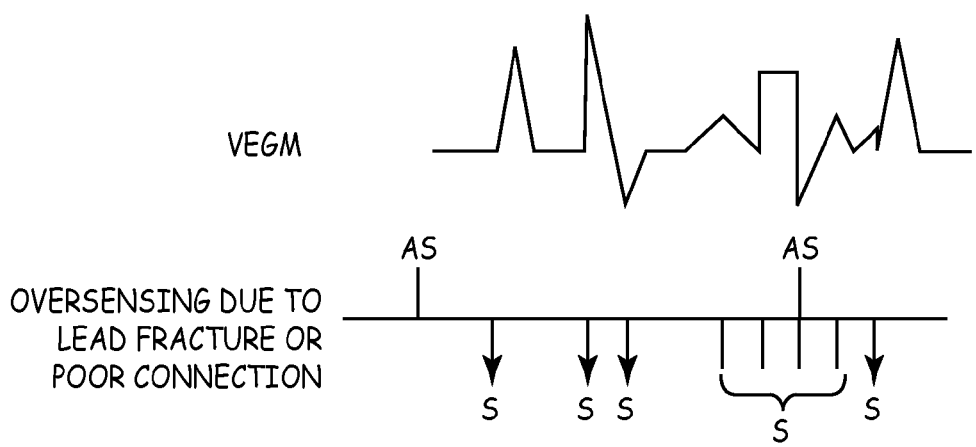
FIG. 2C is an illustration of a ventricular EGM (VEGM) signal with noise due to a lead fracture or poor lead connection and a corresponding marker channel during these types of oversensing.

The entire contents of U.S. patent application Ser. No. 11/108,472, Gunderson et al., Method and Apparatus for Identifying Oversensing Using Far-Field Intracardiac Electrograms and Marker Channels, filed Apr. 18, 2005 (now U.S. Published Patent Application No. 2006/0235476 A1, published Oct. 19, 2006), is incorporated herein by reference.

The following disclosure is presented to enable a person skilled in the art to make and use the invention. Various modifications to the illustrated embodiments will be readily apparent to those skilled in the art, and the generic principles herein may be applied to other embodiments and applications without departing from the spirit and scope of the present invention as defined by the appended claims. Thus, the present invention is not intended to be limited to the embodiments shown, but is to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the invention. Skilled artisans will recognize the examples provided herein have many useful alternatives which fall within the scope of the invention.

For purposes of illustration only, the invention is described below in the context of implantable cardioverter defibrillators ("ICDs"). However, embodiments of the invention are not limited to use with ICDs, and may be employed in other types of implantable cardiac devices such as pacemakers, cardiac resynchronization therapy (CRT) devices, implantable recording devices, and similar systems. Further, embodiments of the invention are described in the context of sensing intrinsic ventricular depolarizations (R-waves) from far-field EGM signals. However, this is by way of illustration and not limitation, as embodiments of the invention may be employed to sense intrinsic atrial depolarizations (P-waves) from far-field EGM signals without departing from the scope of the invention.

Figure 3:
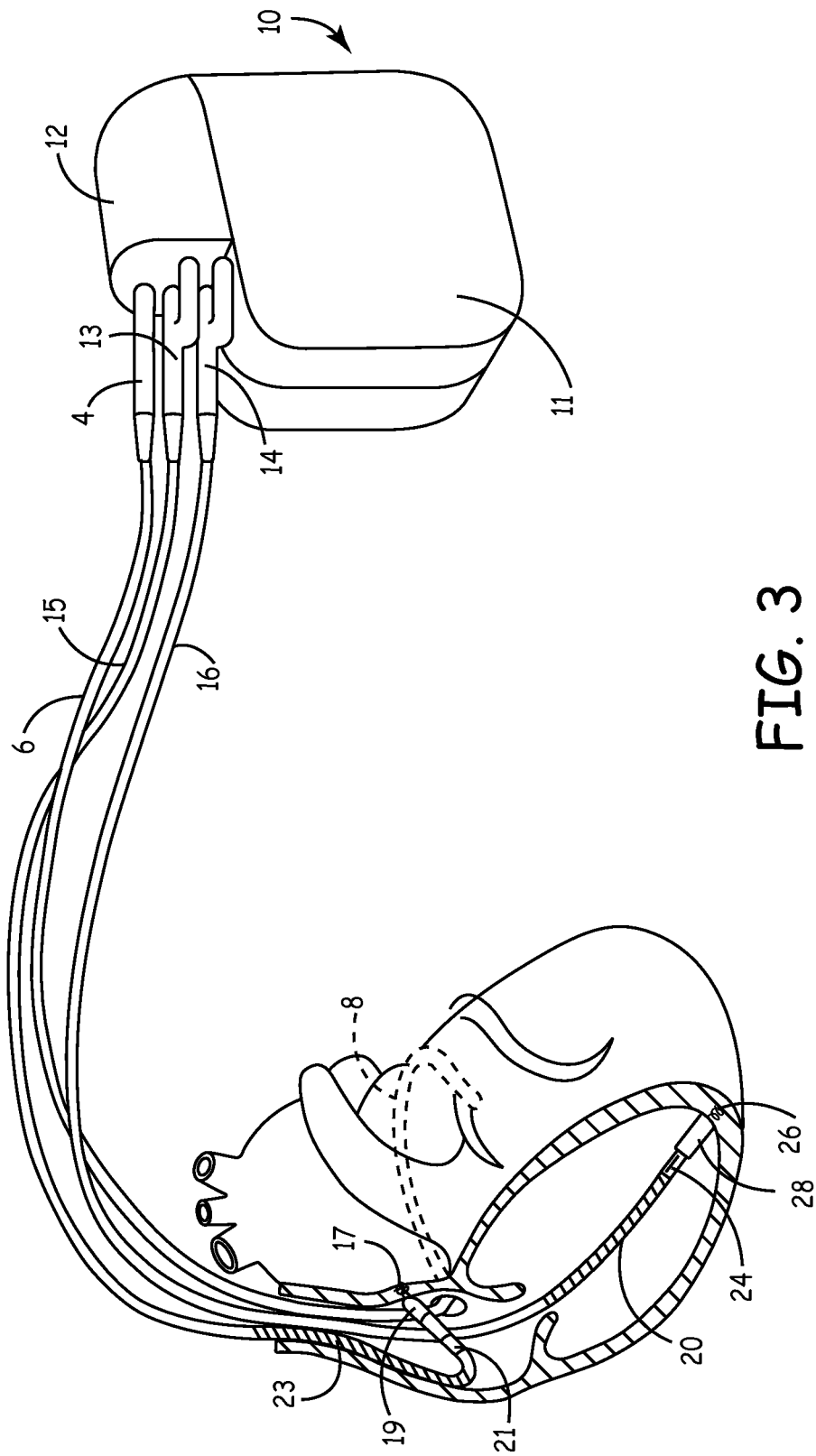
FIG. 3 is an illustration of an implantable cardiac stimulation device capable of pacing, cardioversion, and defibrillation in communication with a heart via stimulation and sensing leads.

An exemplary ICD 10 is shown in FIG. 3, with which methods included in the present invention may be used. The ICD 10 is shown coupled to a heart by way of leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 3, the right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10.

The right atrial lead 15 may be positioned such that its distal end is in the vicinity of the right atrium and the superior vena cava. Lead 15 may be equipped with a ring electrode 21 and an extendable helix electrode 17, mounted retractably within electrode head 19, for sensing and pacing in the right atrium. Lead 15 may be further equipped with a coil electrode 23 for delivering high-energy shock therapy. The ring electrode 21, the helix electrode 17 and the coil electrode 23 may each be connected to an insulated conductor within the body of the right atrial lead 15. Each insulated conductor is coupled at its proximal end to a connector carried by bifurcated connector 13.

A coronary sinus lead 6 may be advanced within the vasculature of the left side of the heart via the coronary sinus and great cardiac vein. The coronary sinus lead 6 is shown in the embodiment of FIG. 3 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 and 23 for defibrillation of the atria or ventricles. It is recognized that alternate lead systems may be substituted for the lead system illustrated in FIG. 3. While a particular multi-chamber ICD and lead system is illustrated in FIG. 3, methodologies included in the present invention may be adapted for use with any single chamber, dual chamber, or multichamber ICD or pacemaker system, or other cardiac monitoring device. A medical device in which the present invention may be usefully practiced may include a subcutaneous cardioverter/defibrillator, for example, as described in commonly assigned U.S. patent application Ser. No. 11/037,123, entitled "Method and Apparatus for Detection in a Medical Device", by Mitrani et al. and filed Jan. 18, 2005 (now U.S. Patent Application Publication No. 2006/0161205A, published Jul. 20, 2006), incorporated by reference in its entirety.

Figure 4:
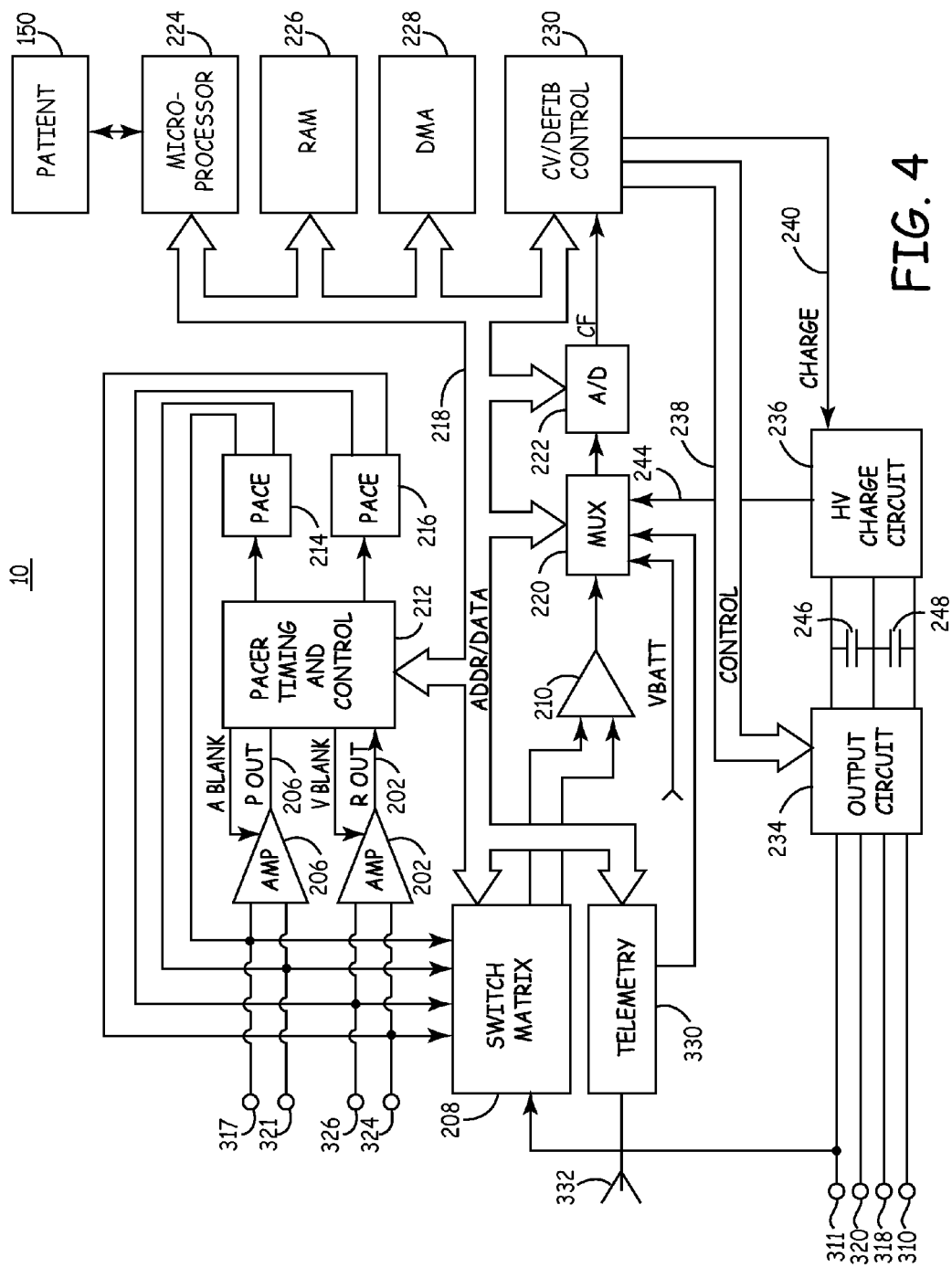
FIG. 4 is a functional block diagram of the implantable pacemaker/cardioverter/defibrillator shown in FIG. 3.

A functional schematic diagram of the ICD 10 is shown in FIG. 4. This diagram should be taken as exemplary of the type of device with which the invention may be embodied and not as limiting. The disclosed embodiment shown in FIG. 4 is a microprocessor-controlled device, but the methods of the present invention may also be practiced with other types of devices such as those employing dedicated digital circuitry.

With regard to the electrode system illustrated in FIG. 3, the ICD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 may take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the heart rhythm employing any of the numerous signal processing methodologies known in the art. A tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, may be stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair may include any of the following exemplary combinations: any pair of defibrillation coil electrodes 8, 20 or 23; any of the defibrillation coil electrodes 8, 20 or 23 with housing 11; a tip electrode 17 or 26 with housing 11; a tip electrode 17 or 26 with a defibrillation coil electrode 20 or 23; or an atrial tip electrode 17 with ventricular ring electrode 24. While these electrode combinations are provided as examples of typically used far-field electrode pairs, the list is by no means exhaustive and extends to any combination of electrodes that provides a signal different from those used for obtaining near-field EGM signals. The use of near-field and far-field EGM sensing of arrhythmia episodes is described in U.S. Pat. No. 5,193,535, issued to Bardy, incorporated herein by reference in its entirety. Annotation of sensed events which may be displayed and stored with EGM data is described in U.S. Pat. No. 4,374,382 issued to Markowitz, incorporated herein by reference in its entirety.

Referring again to FIG. 4, the telemetry circuit 330 may receive downlink telemetry from and may send uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. In accordance with the present invention, EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 4 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated ROM in which stored programs controlling the operation of the microprocessor 224 reside. A portion of the random access memory 226 may be configured as a number of recirculating buffers capable of holding a series of measured intervals for analysis by the microprocessor 224 for predicting or diagnosing an arrhythmia.

In response to the detection of tachycardia, anti-tachycardia pacing therapy can be delivered by loading a regimen from microcontroller 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 5:
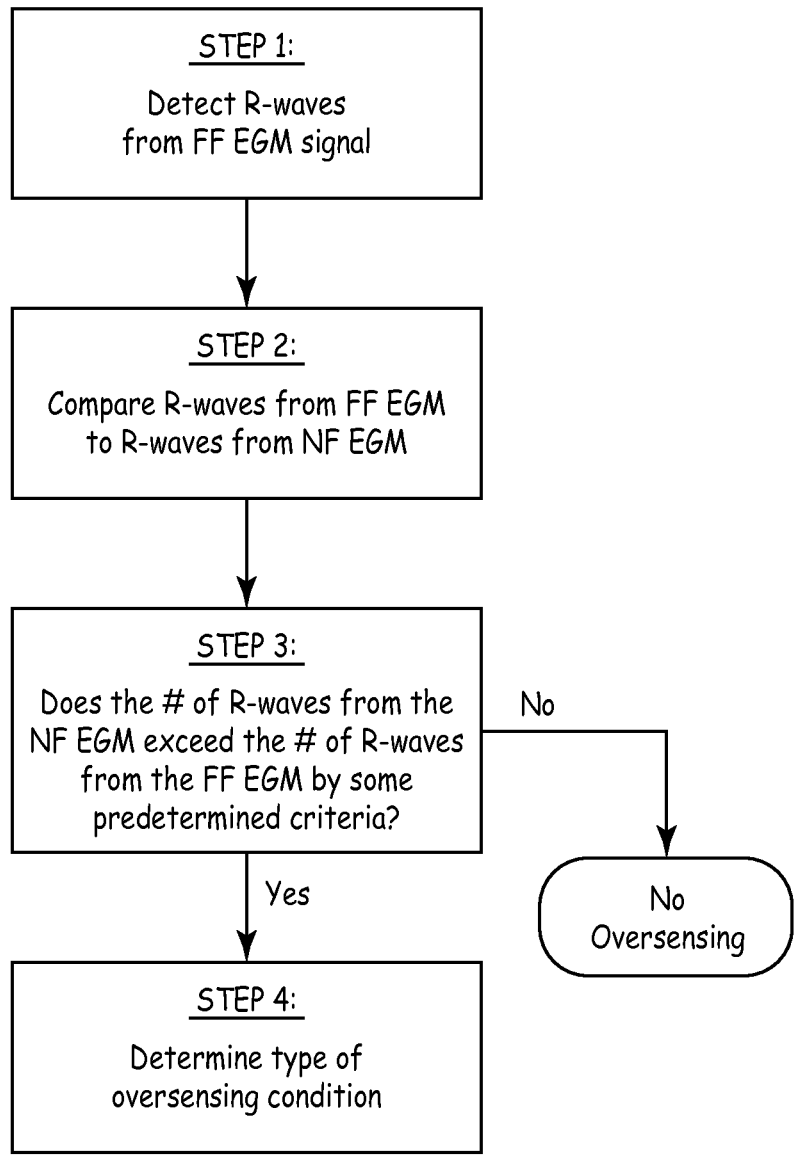
FIG. 5 is a flowchart showing an overview of a method for identifying and classifying oversensing of intrinsic depolarizations.

FIG. 5 is a flowchart that describes an overview of a method of identifying the presence and classifying the type of R-wave oversensing in accordance with an embodiment of the invention. The first step in the method is to detect the occurrence of R-waves from analysis of the far field electrogram (FF EGM) signal. More details on this first step will be provided in a later section. After identifying R-waves from the FF EGM ($V_{S\text{-}FF}$), the method next compares the number of detected $V_{S\text{-}FF}$ events to the number of sensed near-field R-waves ($V_{S\text{-}NF}$) as indicated by the marker channel. The third step is to use the comparison to determine whether oversensing exists, and if so, the fourth step is to determine the type of oversensing.

Figure 6:
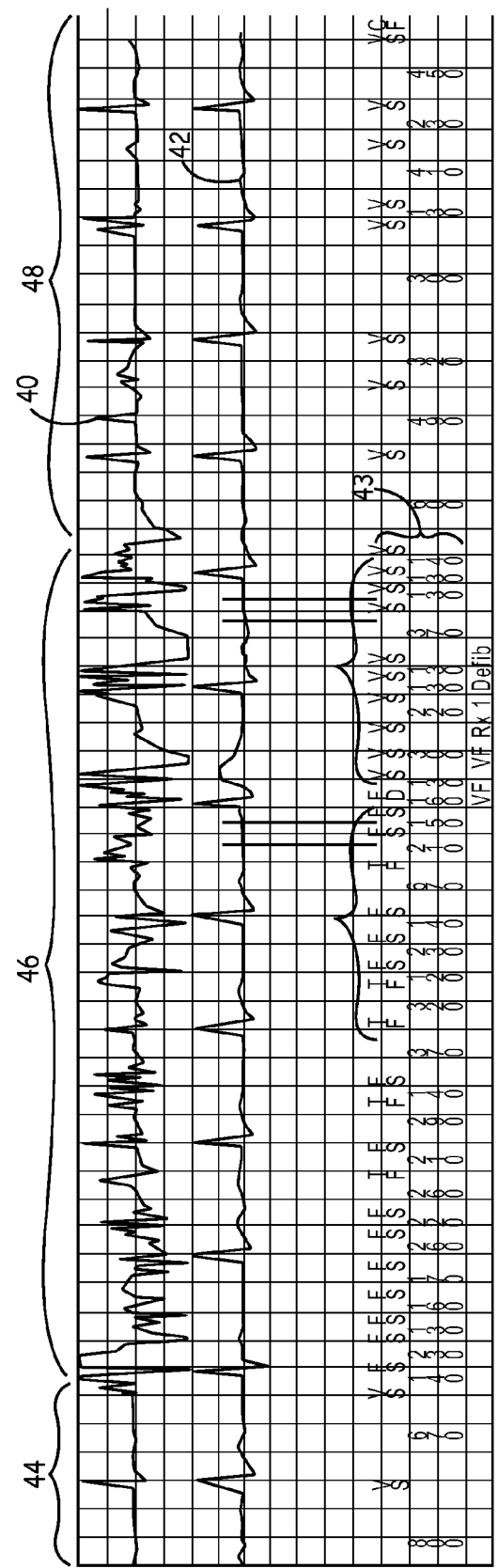
FIG. 6 is a portion of a stored episode signal from an implantable medical device (IMD) showing near-field and far-field EGM signals and corresponding marker channel data.

FIG. 6 is a portion of a stored electrogram showing near-field and far-field EGM signals where there is an indication of false positive near-field events (i.e., oversensing). As illustrated in FIG. 6, the near-field signal 40 may have been recorded between tip and ring electrodes of a bipolar sensing lead, such as electrodes 24 and 26, for example. This signal is input to a sense amplifier that senses voltages that exceed a threshold. The far-field signal 42 is recorded between secondary electrodes such as the lead coil and the can or a sensing lead in another part of the heart. A marker channel 43 below far-field electrogram 42 displays each sensed event from the near-field signal with an annotation, such as Fibrillation Sense (FS), Fibrillation Detected (FD), Tachycardia Sense (TS), Ventricular Sense (VS), Capacitors charged (CE), or Capacitor Discharged (CD) for example. The numbers below the letters on marker channel 43 indicate the time intervals between sensed events. For example, on the left side of FIG. 6, there are two VS events, and the number below and between them is "670," indicating that there were 670 milliseconds between the two VS events. Note that at the left of the near-field electrogram signal 40 is a relatively normal R-wave representation 44. The period of relative normal R-wave representation 44 is followed by a series of erratic signals 46 that may indicate an oversensing problem (i.e., a fractured lead conductor or insulation break on the lead, for example). Note also that the far-field electrogram signal 42 does not exhibit the erratic signal pattern seen on the near-field signal 40.

In certain applications, only the far-field EGM signal is stored in memory, along with the marker channel produces, which an information signal that corresponds to the event timing information provided by the NF EGMs, for example when amplitude threshold criteria are met. Thus, the marker channel may display the effects of oversensing on a near-field channel, which may or may not be present on the corresponding far-field channel.

Figure 7:
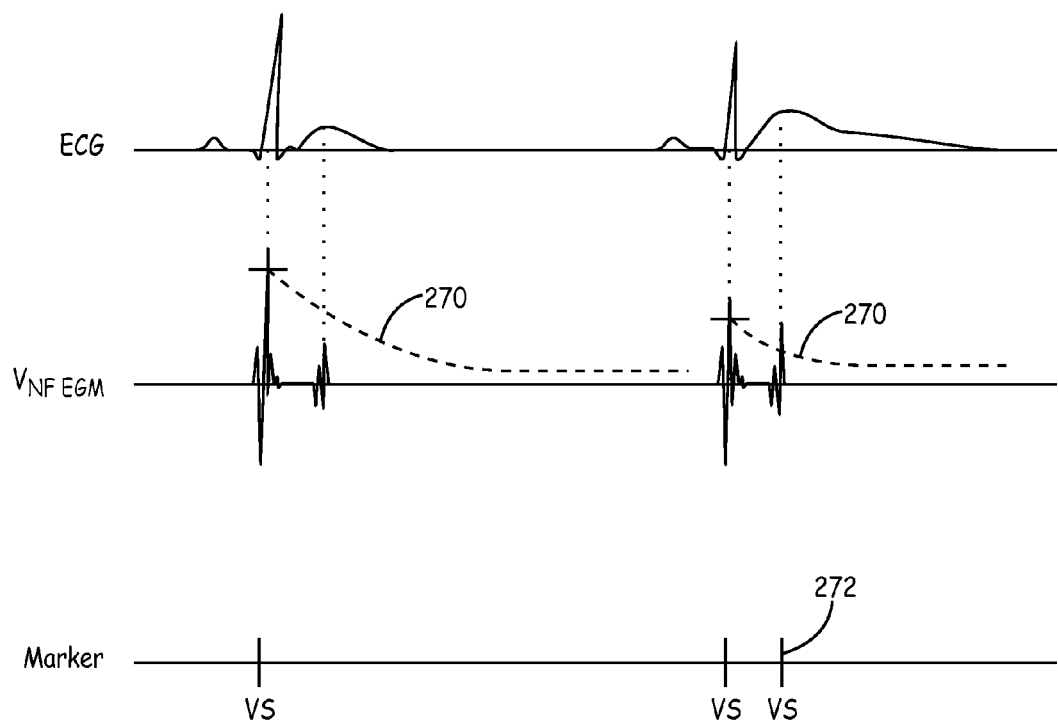
FIG. 7 is an illustration of an auto-adjusting threshold on a ventricular channel.

FIG. 7 is a drawing of an NF V EGM signal and a marker channel signal, with an auto-adjusting sensitivity threshold 270 superimposed in dashed lines on the NF V EGM. The sensitivity threshold 270 shown in FIG. 7 is decreasing in magnitude based on a starting amplitude proportional to the amplitude of the sensed ventricular event. "Auto-adjusting thresholds" are commonly used in ICDs in order to detect both normal amplitude R-waves and smaller amplitude signals associated with ventricular tachycardia and ventricular fibrillation.

On the right-hand side of FIG. 7, the auto-adjusting threshold 270 begins at an amplitude proportional to a relatively small amplitude R-wave. In this case, the threshold 270 has decreased to a level at which detection of the T-wave of the same cardiac cycle is possible. As shown on the marker channel, the detected T-wave is indicated as a sensed ventricular event ($V_S$) 272. In certain situations, the inappropriate sensing of T-waves may result in inappropriate arrhythmia detections. For example, the presence of a sensed T-wave as a ventricular sensed event ($V_S$) may cause the device to see two intervals of relatively short duration, either or both of which may fall within a particular ventricular tachycardia or fibrillation rate zone, and may lead to arrhythmia detection and possibly to therapy delivery. Arrhythmia detection, with or without therapy delivery, will typically result in a recorded device episode, which may be retrieved and analyzed from the IMD by an operator or physician.

Sensing R-Waves from FF EGM Signals: Method No. 1

Figure 8:
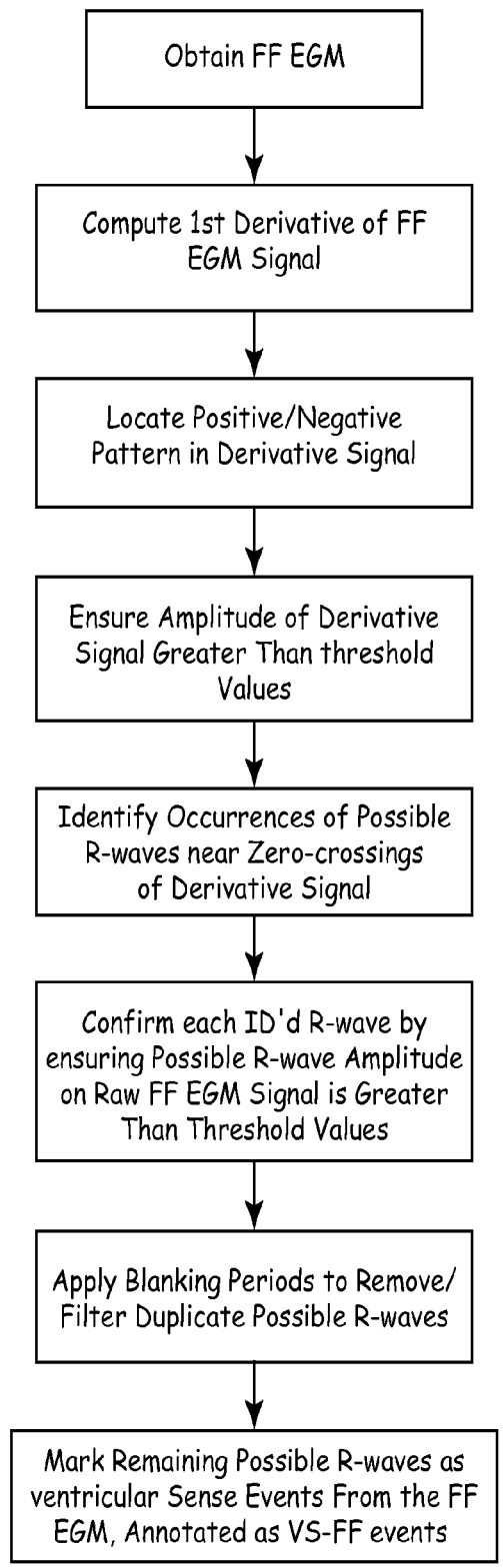
FIG. 8 is a flowchart showing a method of detecting intrinsic depolarizations of a heart chamber by analyzing data from far-field EGM signals in accordance with an embodiment of the invention.
Figure 8A:
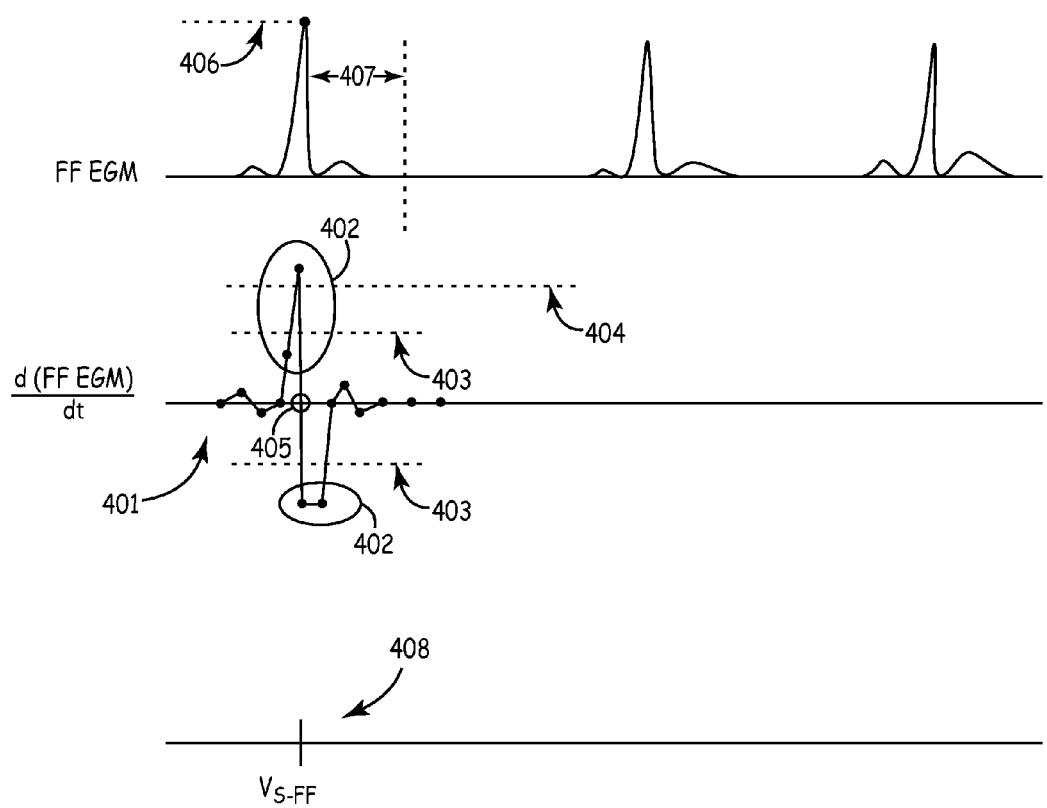
FIG. 8(a) illustrates steps in detecting intrinsic depolarizations from the FF EGM according to the embodiment of the invention described in FIG. 8.

FIG. 8 is a flowchart showing an algorithm for sensing R-waves from a far-field electrogram in accordance with an embodiment of the invention. The first step in detecting R-waves from the far-field electrogram is to obtain a far-field electrogram signal and convert it to a digitally sampled waveform comprising a stream of digital sample points. This may be performed by either an ICD or by external processing means, such as an external programmer for example. The next step is to take the first derivative of the far-field electrogram signal. The first derivative, for example, may be obtained by taking the amplitude of a given FF EGM digital sample, subtracting from it the amplitude of the immediately preceding sample, and dividing the result by the time interval between samples. (The step of dividing the result by the time interval between samples may be unnecessary since the time interval between consecutive samples is typically constant.) FIG. 8(a) graphically illustrates the first derivative signal 401 corresponding to the FF EGM signal, as well as the steps that follow according to an embodiment of the invention.

The next step is to locate a pattern in the derivative signal that shows a change in polarity of the derivative signal.

Changes in the polarity of the derivative signal indicate the "peaks" in the FF EGM signal that may correspond to P-waves, R-waves, T-waves, or other phenomena. In one embodiment, the polarity shift pattern may be identified by two consecutive positive sample points 402 on the derivative signal immediately followed by two negative sample points 402 on the derivative signal. Other similar patterns in the derivative signal may be employed by one having skill in the art to determine points where the derivative signal changes polarity to indicate the presence of a "peak" signal of interest. Additionally, the exact criteria for identifying the change in polarity of the derivative signal may need to be fine-tuned for a particular patient, for example.

The next step in the method of detecting R-waves from FF EGMs is to apply amplitude criteria to the derivative signal sample points satisfying the polarity shift pattern described above. In one embodiment, if the pattern of two positive followed by two negative derivative signals is first satisfied, then the magnitude of the derivative signals that meet the pattern requirement are compared to one or more threshold values to ensure that minimum slope criteria are met. For example, if the pattern determined that two positive followed by two negative derivative sample points was satisfied, the four samples may be analyzed to ensure that a certain number of them meet a minimum threshold 403, thereby ensuring that the slope (derivative) is large enough to warrant further consideration. In one embodiment, three out of the four derivative samples must have an absolute value greater than some predetermined derivative magnitude threshold 403, such as 0.25 mV/ms, for example. The minimum slope criteria may, in some embodiments, further require that the maximum of the four derivative sample point amplitudes be greater than some maximum derivative threshold value 404, such as 0.5 mV/ms, for example.

Where the derivative polarity change pattern and derivative threshold criteria are met, the next step in the method is to identify the zero crossing (polarity change point) of the derivative signal as the location of a possible sensed ventricular depolarization (VS-FF). The zero crossing point 405 is shown in FIG. 8(*a*) as the point in time between the second positive derivative sample and the first negative derivative sample according to one embodiment of the invention.

The next step in the method is to apply amplitude threshold criteria to the possible sensed ventricular depolarizations. In one embodiment, this is accomplished by determining a maximum signal value 406 from the identified possible ventricular depolarizations from the far-field EGM. A far-field EGM threshold 410 is then defined as some percentage of the maximum signal value, for example 50%. Each of the identified possible ventricular depolarizations must next satisfy this amplitude threshold requirement. For example, in one embodiment, each possible VS-FF event must have a signal amplitude on the FF EGM equal to or greater than 50% of the maximum signal value 406, or else it is removed from further consideration as a VS-FF event.

The next step in the method is to apply a blanking period 407 (for example, 180 msec), to the remaining VS-FF events. If any VS-FF event occurs within the blanking period 407 of a preceding VS-FF event, it is removed from further consideration as a VS-FF event. At this point, all of the VS-FF events have thus been sensed or detected according to an embodiment of the invention, and may be annotated as a VS-FF event 408 on a corresponding marker channel, for example.

Sensing R-Waves from FF EGM Signals: Method No. 2

Figure 9:
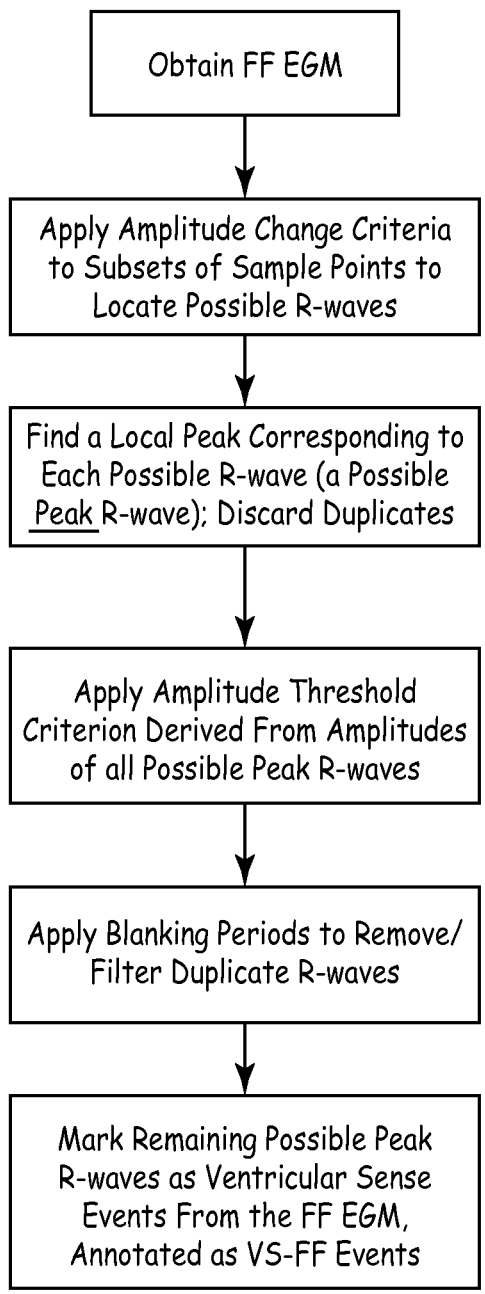
FIG. 9 is a flowchart showing a method of detecting intrinsic depolarizations of a heart chamber by analyzing data from far-field EGM signals in accordance with an embodiment of the invention.

In an alternate embodiment of the invention, a method of sensing R-waves from the far-field EGM may be performed according to the steps shown in FIG. 9. The first step again involves obtaining a FF EGM signal and converting it to a digital waveform comprising a stream of digital sample points.

Starting at the beginning of the stored FF EGM, subsets (windows) of the stream of digital sample points are evaluated to identify which subsets satisfy amplitude change criteria (based on changes in the amplitude of the signal) to identify "possible" R-waves. For example, an embodiment of the invention may evaluate subsets comprising 3 sample points, $V_1$–$V_3$, according to the following amplitude change criteria:

IF ($V_2$–$V_1 \geq 0.6$ AND $V_3$–$V_2 \geq 0.6$)

OR ($V_2$–$V_1 \leq -0.6$ AND $V_3$–$V_2 \leq -0.6$)

OR (ABSOLUTE VALUE OF $|V_3$–$V_2$+$V_2$–$V_1| \geq 1.18$)

THEN Mark $V_1$ as a "possible" R-wave (to be evaluated further).

The subsets may contain more than 3 sample points, however 3 of the sample points within the subset are evaluated according to the above criteria. Also, the choice of V1 as the point to "mark" as a possible R-Wave is somewhat arbitrary and a different point may be chosen by one of ordinary skill in the art to mark the location of a possible R-wave. Lastly, the values 0.6, –0.6, and 1.18 represent exemplary first, second, and third specified amounts. One of ordinary skill in the art will recognize that the actual values used may be altered from the above examples to accommodate varying signal strengths and to vary the nature of the amplitude change criteria. Such modification is contemplated and is considered to fall within the scope of the invention.

After evaluating a given subset, or window, of sample points, the window is shifted one sample point in time to the next window of sample points. In the preceding example, the second window would consist of the second, third, and fourth sample points of the stored FF EGM. The amplitude change criteria are applied to this window of sample points to evaluate whether the second sample point of the stored FF EGM should be marked as a "possible" R-wave. This process of shifting or scrolling the windows continues until all of the windows in the stored FF EGM have been evaluated and all "possible" R-waves have been identified. FIG. 9(*a*) shows examples of subsets that may satisfy the above-described amplitude change criteria to identify "possible" R-waves 502.

The next step in the algorithm is to find a "local peak" in the stored FF EGM signal that corresponds to each of the "possible" R-waves 502 identified in the previous step. For example, in one embodiment of the invention, a "local peak" is sought by evaluating a frame 501 (FIG. 9(*a*)) of sample points surrounding and including each "possible" R-wave 502 to identify the sample point within frame 501 having the largest absolute value as a "possible peak" R-wave 504. Frame 501 may, for example, comprise eight consecutive sample points immediately preceding and eight consecutive sample points immediately following each of the "possible" R-waves, as well as the "possible" R-wave itself. (The choice of the number of surrounding sample points to search is a matter of design; a smaller or larger number may be selected without departing from the scope of the invention.) The above process is repeated until a "possible peak" R-wave 504 is identified corresponding to each "possible" R-wave 502 in the stored FF EGM signal. It should be noted, as indicated by FIG. 9(*a*), that two or more "possible" R-waves 502 processed in this manner may identify the same "possible peak"

R-wave 504. Duplicate "possible peak" R-waves thus identified are considered to be a single "possible peak" R-wave. As a result, there may be fewer "possible peak" R-waves than "possible" R-waves.

The next two steps of the algorithm may be performed in any order, the goal being to remove from further consideration those "possible peak" R-waves 504 which are deemed to be either too small in amplitude, or which occur too soon after another R-wave to be classified as a separate ventricular event. For purposes of illustration, an embodiment of the invention is described below in which the amplitude criterion is applied first. One of ordinary skill in the art will appreciate that the order of these steps may be reversed without departing from the scope of the invention.

Figure 9A:
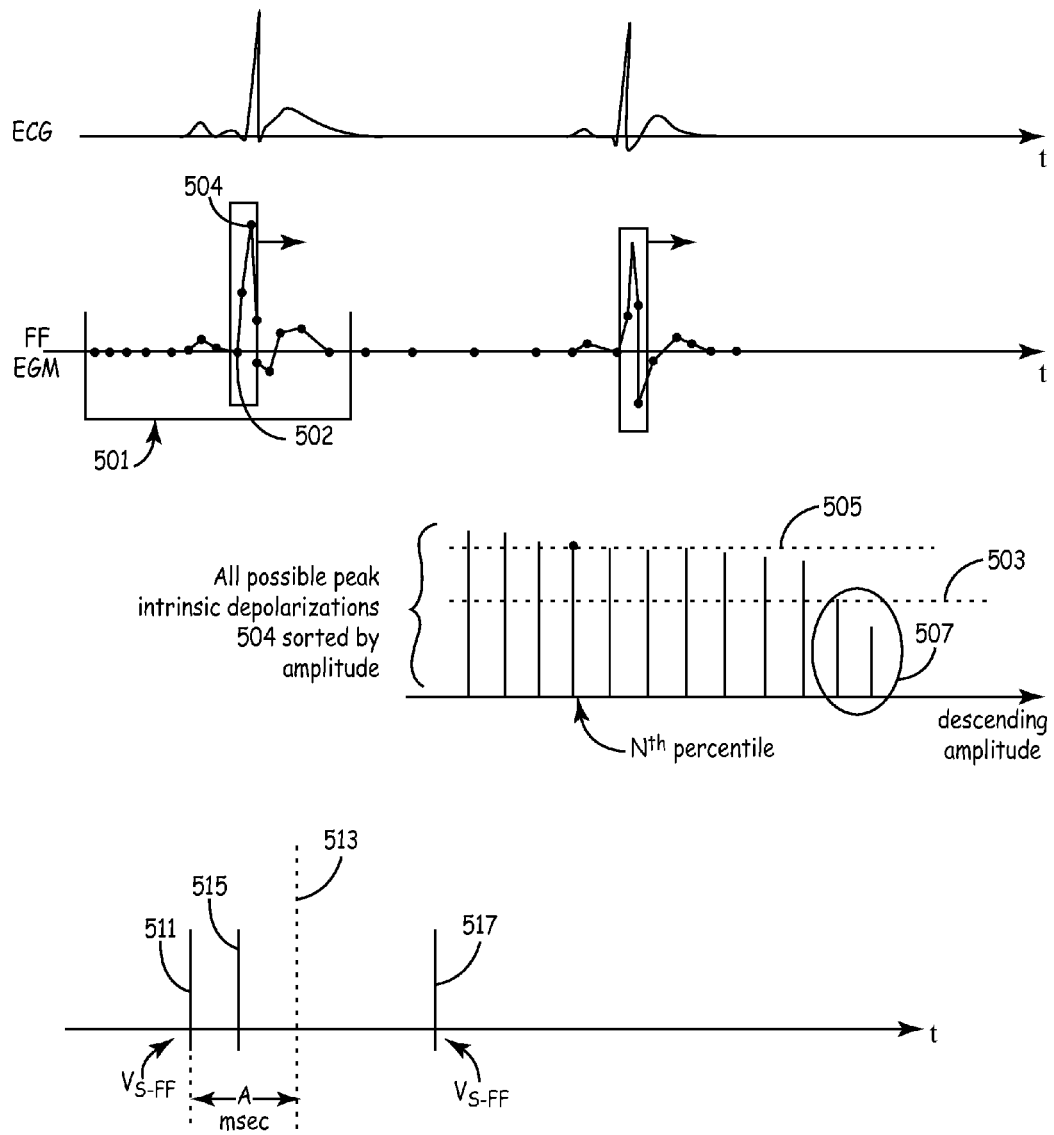
FIG. 9(a) illustrates steps in detecting intrinsic depolarizations from the FF EGM according to the embodiment of the invention described in FIG. 9.

To apply the amplitude criterion, all "possible peak" R-waves 504 are evaluated against an amplitude threshold criterion 503, and those with amplitudes below the threshold are removed from further consideration. In some embodiments of the invention, the amplitude threshold criterion 503 itself may be derived from analysis of all the measured "possible peak" R-wave amplitudes. In one embodiment, for example, the amplitude threshold criterion 503 may be derived from a representative amplitude associated with the "possible peak" R-wave at a specified ("$N^{th}$") percentile rank (the $75^{th}$ percentile, for example) based on amplitude sorting. FIG. 9(a) shows the derivation of an amplitude threshold criterion 503 that involves selecting the "possible peak" R-wave at the $N^{th}$ percentile (based on amplitude), and multiplying the amplitude 505 of that sample point by a scaling factor or fraction (0.57, for example) to obtain the amplitude threshold criterion 503. Using these or other similar amplitude threshold criteria may "filter" out relatively small amplitude signals 507 that may have satisfied the "possible" R-wave and "possible peak" R-wave criteria, but may be manifestations of events other than ventricular contractions (such as T-wave oversensing, R-wave double-counting, noise, etc.). These other types of events typically have amplitudes that are smaller than most ventricular sensed events. FIG. 9(a) shows a number of such signals 507 being filtered out by the above-described amplitude threshold criterion 503 and are thus removed from further analysis (i.e., removed from further consideration as possible R-waves).

FIG. 9(a) also illustrates the above-mentioned step of filtering out "possible peak" R-waves that occur too soon after a preceding R-wave. According to one embodiment of the invention, the earliest occurring "possible peak" R-waves in the FF EGM signal are analyzed first, proceeding chronologically throughout the FF EGM signal. For example, in FIG. 9(a), the earliest occurring "possible peak" R-wave 511 is analyzed first. If a second "possible peak" R-wave 515 occurs within some defined blanking period 513 of "A" msec, for example 180 msec, after the "possible peak" R-wave 511 being analyzed, it is removed from further consideration. The method continues by evaluating the next "possible peak" R-wave that occurs, for example R-wave 517 in FIG. 9(a).

Figure 9B:
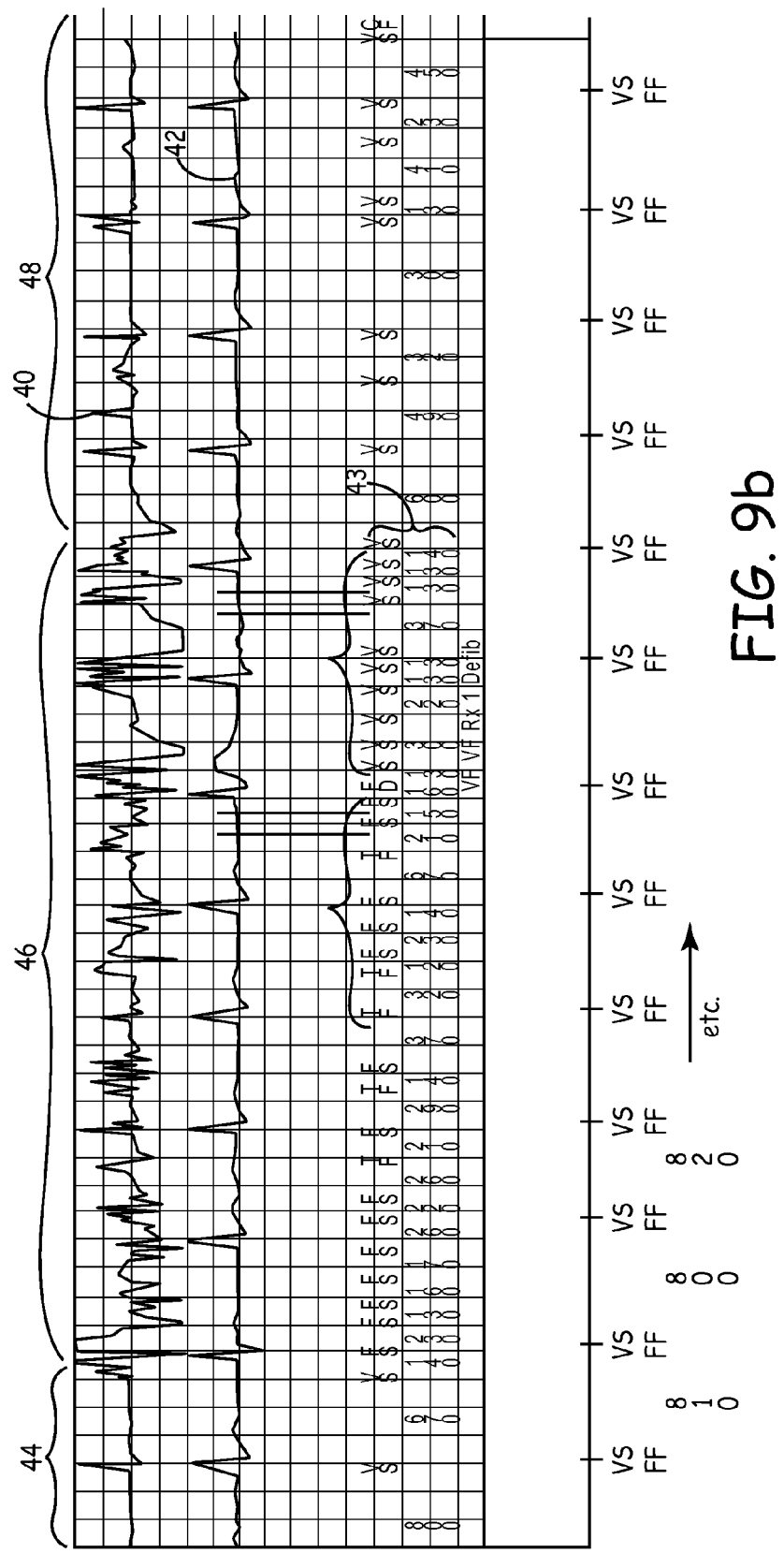
FIG. 9(b) illustrates a portion of a stored episode signal from an implantable medical device (IMD) showing near-field and far-field EGM signals and corresponding NF and FF marker channel data using an annotation scheme in accordance with an embodiment of the invention.

Once all of the "possible peak" R-waves have been evaluated against the amplitude threshold and blanking interval criteria described above, the remaining R-waves are classified as ventricular sensed events on the FF EGM, or "VS-FF events," according to an embodiment of the invention, and may be labeled or annotated as such on a marker channel as indicated in FIG. 9(a). To distinguish between marker channel indications of ventricular sensed events derived from near-field EGMs versus far-field EGMs, an annotation scheme may be employed to reflect this difference, such as $V_{S\text{-}NF}$ and/or $V_{S\text{-}FF}$. An example of one possible type of annotation scheme is provided in FIG. 9(b).

Either of the methods described above for detecting R-waves from a FF EGM signal may be employed to obtain the input to the method described below for determining the existence and type of oversensing. Minor modifications to the techniques described above may be apparent to one of ordinary skill in the art and should be considered to fall within the scope of the invention.

Method of Classifying the Type of Oversensing

Figure 10:
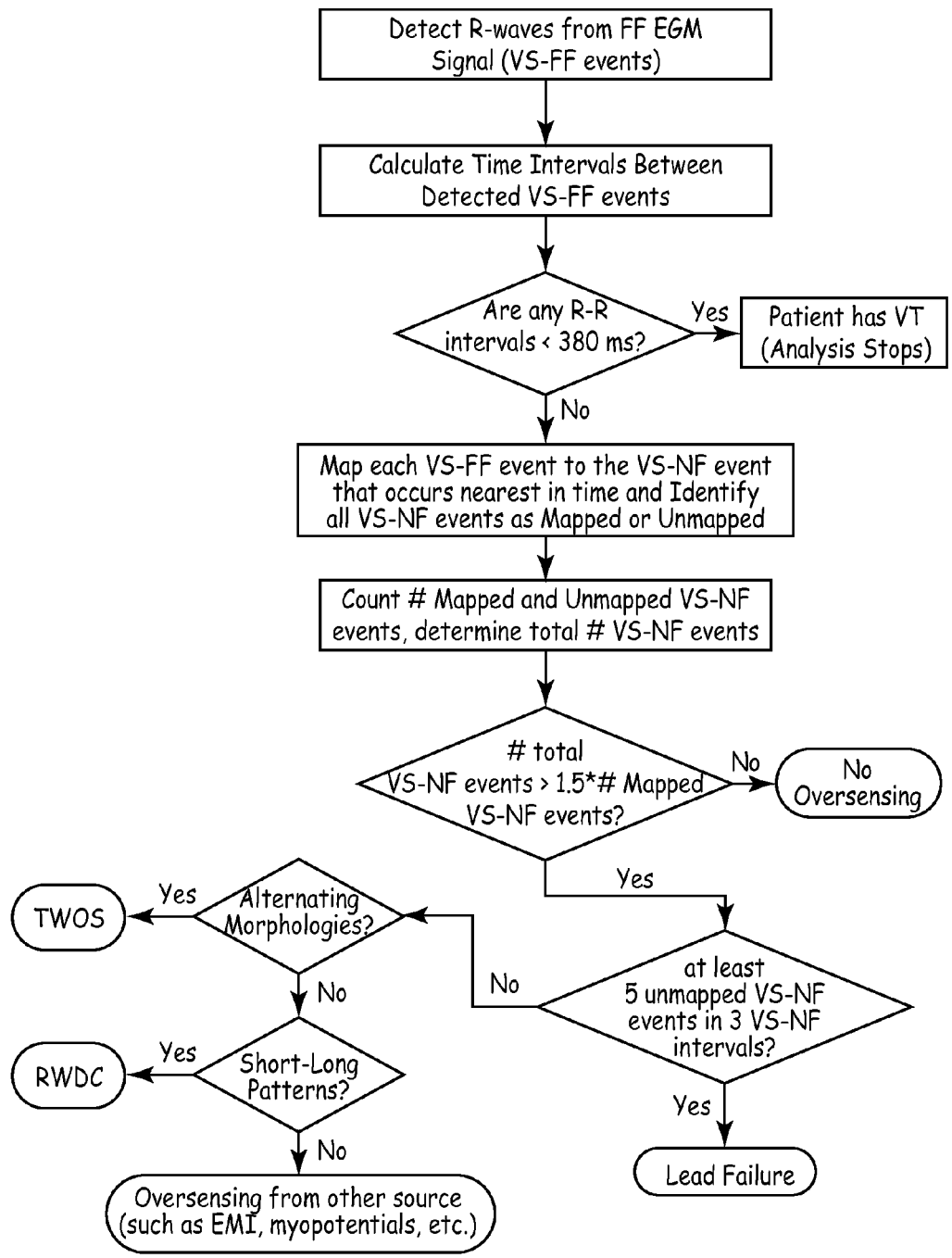
FIG. 10 is a flowchart showing a method for identifying and classifying oversensing of intrinsic depolarizations in accordance with an embodiment of the invention.

FIG. 10 is a flowchart describing a method for using sensed R-waves derived from FF EGMs to analyze potential oversensing by near-field EGMs as indicated by marker channels. The first step in the method is to measure the R-R intervals between the sensed R-waves from the FF EGM signal (i.e., the VS-FF event intervals). If any of the intervals between VS-FF events is less than some predetermined criteria (for example, less than about 330-400 msec), then a ventricular tachycardia is deemed to exist and no further analysis of oversensing is performed.

If all of the intervals between VS-FF events is greater than the predetermined criteria, then the next step is to "map" the VS-FF events to the ventricular sense events from the near-field EGM (the VS-NF events), as identified by the marker channel. Mapping the two sets of detected R-waves may involve identifying a single VS-NF event that most closely corresponds in time to each VS-FF event. For example, the nearest VS-NF event that occurs within plus or minus "M" msec, for example 100 msec, of each VS-FF event may be identified as being a "mapped" VS-NF event. Therefore, any VS-NF events not identified as being "mapped" VS-NF events are considered to be the result of an oversensing condition; the designation "unmapped" will be used to distinguish such VS-NF events from mapped VS-NF events.

Figure 11:
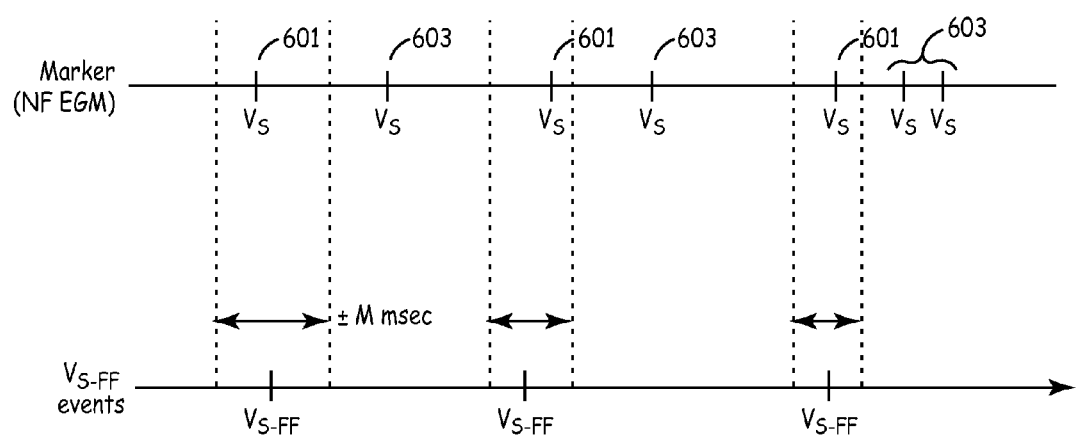
FIG. 11 shows the step of mapping R-waves detected from far-field EGMs to R-waves detected from near-field EGMs according to an embodiment of the invention.

FIG. 11 shows a comparison of the VS-FF events to the VS-NF events. FIG. 11 further shows the mapping of VS-FF events to VS-NF events to determine true (mapped) VS-NF events 601 versus oversensed (unmapped) VS-NF events 603. The next step in the method is to determine whether the amount of oversensing exceeds some preset minimum criteria. For example, in FIG. 10, a multiple (such as 1.5, for example) may be applied to the number of mapped VS-NF events 601 to determine if oversensing is present. If the total number of VS-NF events (i.e., mapped plus unmapped VS-NF events) does not exceed the number of mapped VS-NF events by the preset multiple (by a factor of 1.5 in this example), then the method determines that no oversensing (or an insignificant amount of oversensing) exists. If the total number of VS-NF events exceeds the predetermined multiple of mapped VS-NF events, then the method determines that oversensing exists and attempts to identify the type of oversensing condition.

The method next analyzes whether the oversensing condition is due to lead fracture/lead failure or a poor lead connection. For example, in the embodiment illustrated in FIG. 10, if there are five or more unmapped VS-NF events that fall within any three mapped VS-NF event intervals, the method determines that the oversensing is due to a lead fracture/lead failure or a poor lead connection. This is because lead failure and connection problems typically result in intermittent bursts of signal energy. If the method determines that the oversensing is not a result of lead failure or a poor lead connection, the next step is to analyze whether there are alternating morphologies that may be indicative of T-wave oversensing. Reference is made to U.S. patent application Ser. No. 10/418,857 entitled "Method and Apparatus for Identifying Cardiac and Non-cardiac Oversensing Using Intracardiac Electrograms," to Gunderson, et al. (now U.S. Published Patent Application No. 2004/0015197 A1), herein incorporated by reference in its entirety. If alternating morphologies are determined to be present, then the method determines that the oversensing is due to T-wave oversensing.

If the method determines that T-wave oversensing is not present, then the method next looks for the presence of a short-long interval pattern between mapped and unmapped VS-NF events, for example 130 msec-340 msec, 120 msec-330 msec, 130 msec-350 msec. If a short-long interval pattern is detected, the method determines that the oversensing is due to R-wave double-counting. If the method determines that oversensing is not the result of R-wave double-counting, then the method indicates that the oversensing is possibly due to a variety of other potential causes (such as EMI, myopotentials, etc.).

When methods included in the present invention for recognizing oversensing are implemented in an external device, EGM data that has been stored in an implanted device in response to an arrhythmia detection or other monitoring algorithm may be uplinked to the external device. The EGM data is analyzed, and, if oversensing is identified, a report may be generated to notify a physician of the incidence of oversensing and its likely cause. The report may optionally recommend a corrective action for eliminating the oversensing based on the type of oversensing detected.

When methods included in the present invention are implemented in an implantable device, such as an ICD or pacemaker, the EGM analysis may be performed in response to a triggered storage of an EGM episode or on a periodic basis to detect oversensing. Recognition of an oversensing problem may trigger any of a number of responsive actions. A warning flag may be generated to alert a physician of an oversensing problem the next time a device interrogation is performed. A patient notification signal may be generated to notify the patient to seek medical attention for correcting the oversensing problem. A corrective action may also be taken automatically by the implanted device to eliminate oversensing, such as by automatically adjusting a sensitivity setting or changing a sensing electrode configuration.

EGM analysis may also be performed in real-time when methods and apparatus included in the present invention are incorporated in an implantable device. The diagnosis of oversensing in real time may trigger storage of EGM data as well as generate a warning flag and/or a patient notification signal. A corrective action may also be automatically taken by the implanted device in order to eliminate the oversensing. In an ICD, recognition of oversensing allows identification of inappropriate arrhythmia detections due to oversensing. If an arrhythmia detection is determined to be inappropriate, a scheduled anti-arrhythmia therapy may optionally be withheld. Alternatively, the arrhythmia therapy may still be delivered but with a patient notification signal so that the patient will seek medical attention to correct the oversensing problem.

Aspects of the present invention, which allow automatic identification of oversensing, can save a physician considerable time and, moreover, prevent inappropriate arrhythmia detections from going unnoticed. Once oversensing is identified and its probable cause diagnosed, prompt corrective action may be taken so that accurate sensing of heart rhythms may be achieved and appropriate stimulation therapies delivered only as needed. Repeated delivery of unnecessary cardioversion or defibrillation therapies in response to inappropriate arrhythmia detections due to oversensing may be avoided. The methods included in the invention may be implemented in a central computer system, a network or web-based system, allowing a physician to remotely diagnose an oversensing problem. Alternatively, the methods and apparatus included in the present invention may be implemented in an implanted device so that corrective action may be performed automatically to eliminate oversensing.

Thus, embodiments of the method and apparatus for identifying oversensing using far-field intracardiac electrograms and marker channels are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical system comprising:
   at least one implantable lead that includes a plurality of electrodes;
   an implantable medical device coupled to the at least one implantable lead, the implantable medical device including:
   a memory configured to store a near-field electrogram signal and a far-field electrogam signal; and
   a microprocessor configured to obtain the near-field electrogram signal, analyze the near-field electrogram signal to detect sense events in the near-field electrogram signal, obtain the far-field electrogram signal, analyze the far-field electrogram signal to detect sense events in the far-field electrogram signal, map each detected sense event in the far-field electrogram signal to a corresponding detected sense event in the near-field electrogram signal, determine that oversensing exists when a first predetermined number of detected sense events in the near-field electrogram signal that are not mapped to corresponding detected sense events in the far-field electrogram signal occur within a second predetermined number of detected sense events in the near-field electrogram signal that are mapped to corresponding detected sense events in the far-field electrogram signal.

2. The implantable medical system of claim 1, wherein the microprocessor maps each detected sense event in the far-field electrogram signal to a corresponding detected sense event in the near-field electrogram signal that occurs most closely in time.

3. The implantable medical system of claim 1, wherein the microprocessor maps each detected sense event in the far-field electrogram signal to a corresponding detected sense event in the near-field electrogram signal that occurs within plus or minus a predetermined number milliseconds from the detected sense event in the far-field electrogram signal.

4. An implantable medical system comprising:
   at least one implantable lead that includes a plurality of electrodes;
   an implantable medical device coupled to the at least one implantable lead, the implantable medical device including:
   a memory configured to store a near-field electrogram signal and a far-field electrogam signal; and
   a microprocessor configured to obtain the near-field electrogram signal, analyze the near-field electrogram signal to detect sense events in the near-field electrogram signal, obtain the far-field electrogram signal, analyze the far-field electrogram signal to detect sense events in the far-field electrogram signal, map each detected sense event in the far-field electrogram signal to a corresponding detected sense event in the near-field electrogram signal, determine a number of detected sense events in the near-field electrogram signal, determine a number of mapped detected sense events in the near-field electrogram signal, compare the total number of detected sense events in the near-field electrogram signal to a threshold value, the threshold value being determined as a function of the number of mapped detected sense events in the near-field electrogram signal, and determine that oversensing exists when the total number of detected sense events in the near-field electrogram signal is greater than the threshold value and a first predetermined number of detected sense events in the near-field electrogram signal that are not mapped to corresponding detected sense events in the far-field electrogram signal occur within a second predetermined number of detected sense events in the near-field electrogram signal that are mapped to corresponding detected sense events in the far-field electrogram signal.

5. A method comprising:
 obtaining, with a microprocessor, a near-field electrogram signal;
 analyzing the near-field electrogram signal to detect sense events in the near-field electrogram signal;
 obtaining, with the microprocessor, a far-field electrogam signal;
 analyzing the far-field electrogram signal to detect sense events in the far-field electrogram signal;
 mapping, with the microprocessor, each detected sense event in the far-field electrogram signal to a corresponding detected sense event in the near-field electrogram signal; and
 determining, with the microprocessor, that oversensing exists when a first predetermined number of detected sense events in the near-field electrogram signal that are not mapped to corresponding detected sense events in the far-field electrogram signal occur within a second predetermined number of detected sense events in the near-field electrogram signal that are mapped to corresponding detected sense events in the far-field electrogram signal.

6. The method of claim 5, wherein mapping each detected sense event in the far-field electrogram signal to a corresponding detected sense event in the near-field electrogram signal comprises mapping, with the microprocessor, each detected sense event in the far-field electrogram signal to a corresponding detected sense event in the near-field electrogram signal that occurs most closely in time.

7. The method of claim 5, wherein mapping each detected sense event in the far-field electrogram signal to a corresponding detected sense event in the near-field electrogram signal comprises mapping, with the microprocessor, each detected sense event in the far-field electrogram signal to a corresponding detected sense event in the near-field electrogram signal that occurs within plus or minus a predetermined number milliseconds from the detected sense event in the far-field electrogram signal.

8. A method comprising:
 obtaining, with a microprocessor, a near-field electrogram signal;
 analyzing the near-field electrogram signal to detect sense events in the near-field electrogram signal;
 obtaining, with the microprocessor, a far-field electrogam signal;
 analyzing the far-field electrogram signal to detect sense events in the far-field electrogram signal;
 mapping, with the microprocessor, each detected sense event in the far-field electrogram signal to a corresponding detected sense event in the near-field electrogram signal;
 determining, with the microprocessor, a number of detected sense events in the near-field electrogram signal;
 determining, with the microprocessor, a number of mapped detected sense events in the near-field electrogram signal;
 comparing, with the microprocessor, the total number of detected sense events in the near-field electrogram signal to a threshold value, the threshold value being determined as a function of the number of mapped detected sense events in the near-field electrogram signal; and
 determining that oversensing exists when the total number of detected sense events in the near-field electrogram signal is greater than the threshold value and a first predetermined number of detected sense events in the near-field electrogram signal that are not mapped to corresponding detected sense events in the far-field electrogram signal occur within a second predetermined number of detected sense events in the near-field electrogram signal that are mapped to corresponding detected sense events in the far-field electrogram signal.

\* \* \* \* \*

UNITED STATES PATENT AND TRADEMARK OFFICE
CERTIFICATE OF CORRECTION

| | | |
|---|---|---|
| PATENT NO. | : 8,792,971 B2 | Page 1 of 1 |
| APPLICATION NO. | : 13/668673 | |
| DATED | : July 29, 2014 | |
| INVENTOR(S) | : Bruce D. Gunderson et al. | |

It is certified that error appears in the above-identified patent and that said Letters Patent is hereby corrected as shown below:

In the Claims

Claim 1, Column 16, line 20, delete "… signal and a far-field electrogam signal; …" and insert in place thereof -- "… signal and a far-field electrogram signal; …" --

Claim 4, Column 16, line 56, delete "… signal and a far-field electrogam signal; …" and insert in place thereof -- "… signal and a far-field electrogram signal; …" --

Claim 5, Column 17, line 22, delete "… the microprocessor, a far-field electrogam; …" and insert in place thereof -- "… the microprocessor, a far-field electrogram signal; …" --

Claim 8, Column 18, line 15, delete "… the microprocessor, a far-field electrogam; …" and insert in place thereof -- "… the microprocessor, a far-field electrogram signal; …" --

Signed and Sealed this
Sixth Day of January, 2015

Michelle K. Lee
*Deputy Director of the United States Patent and Trademark Office*